(12) United States Patent
Stahl et al.

(10) Patent No.: US 8,557,794 B2
(45) Date of Patent: Oct. 15, 2013

(54) IMMUNEMODULATING OLIGOSACCHARIDES

(75) Inventors: Bernd Stahl, Rosbach (DE); Laura M'Rabet, Amersfoort (NL); Arjan Paul Vos, Bennekom (NL); Johan Garssen, Nieuwehein (NL); Günther Boehm, Echzell (DE)

(73) Assignee: N.V. Nutricia, Zoetermeer (NL)

( * ) Notice: Subject to any disclaimer, the term of this patent is extended or adjusted under 35 U.S.C. 154(b) by 547 days.

(21) Appl. No.: 10/576,834

(22) PCT Filed: Oct. 25, 2004

(86) PCT No.: PCT/NL2004/000750
§ 371 (c)(1),
(2), (4) Date: Apr. 24, 2006

(87) PCT Pub. No.: WO2005/039597
PCT Pub. Date: May 6, 2005

(65) Prior Publication Data
US 2007/0098762 A1    May 3, 2007

(30) Foreign Application Priority Data

Oct. 24, 2003 (EP) .................................. 03078375
Jun. 25, 2004 (EP) .................................. 04076877

(51) Int. Cl.
*A61K 31/715* (2006.01)
(52) U.S. Cl.
USPC ................ 514/54; 514/61; 514/53; 514/58; 536/123.1
(58) Field of Classification Search
USPC .................. 514/54, 61, 53, 58; 536/123.1
See application file for complete search history.

(56) References Cited

U.S. PATENT DOCUMENTS

| 4,412,946 | A | 11/1983 | Zalisz et al. |
| 6,573,245 | B1 | 6/2003 | Marciani |
| 6,576,251 | B1 | 6/2003 | Stahl et al. |
| 2003/0022863 | A1 * | 1/2003 | Stahl et al. ............ 514/54 |

FOREIGN PATENT DOCUMENTS

| DE | 4223613 C2 | 1/1994 |
| EP | 0406685 | 1/1999 |
| EP | 1321527 * | 6/2003 |
| FR | 2781673 | 2/2000 |
| GB | 1327740 | 8/1973 |
| JP | 58004724 | 1/1983 |
| JP | 62270532 | 11/1987 |
| JP | 4300888 | 10/1992 |
| JP | 6256208 | 9/1994 |
| JP | 8092303 | 4/1996 |
| JP | 09048732 | 2/1997 |
| JP | 09208474 | 8/1997 |
| JP | 2003221339 A * | 8/2003 |
| KR | 9711556 B | 7/1997 |
| KR | 2002094725 | 12/2002 |
| WO | WO 85/05031 * | 11/1985 |
| WO | 0008948 | 2/2000 |
| WO | WO 00/57727 | 10/2000 |
| WO | WO 01/33975 A1 | 5/2001 |
| WO | 0160378 A2 | 8/2001 |
| WO | WO 01/60378 A2 | 8/2001 |
| WO | WO 02/042484 A3 | 5/2002 |
| WO | WO 02/47703 A2 | 6/2002 |
| WO | WO 2005/039597 A3 | 5/2005 |

OTHER PUBLICATIONS

Abstract of Ikemizu et al.; JP 2003221339 A, Aug. 5, 2003 (Abstract Sent).*
Nagura et al (British Journal of Nutrition (2002), 88, 421-426).*
Miniello et al. (Acta paediatrica (Oslo, Norway : 1992). Supplement, (Sep. 2003) vol. 91, No. 441, pp. 68-760)(Abstract sent).*
Database WPI, Section Ch, Week 198307, Derwent Publications Ltd., London, GB; Class A96, AN 1983-16545K, XP002277416, & JP 58 004724 A (Meiji Milk Prod Co LTD), Jan. 11, 1983, Abstract.
Database WPI, Section Ch, Week 200332, Derwent Publications Ltd., London, GB; Class B03, AN 2003-339110, XP002277417, & KR 2002094725 A (KT & G Co LTD), 82 Dec. 2002, Abstract.
Database WPI, Section Ch, Week 199249, Derwent Publications Ltd., London, GB; Class A96, AN 1992-403412, XP002277418, & JP 040300888A (Dainippon Ink & Chem KK), Oct. 23, 1992, Abstract.
Database WPI, Section Ch, Week 199441, Derwent Publications Ltd., London, GB; Class B04, AN 1994-329946; XP002277419, & JP 06 256208 A, (Food Design Gijutsu Kenkyu Kumiai), Apr. 9, 1996, Abstract.
Database WPI, Section Ch, Week 199624, Derwent Publications Ltd., London, GB; Class B04, AN 1996-236112, XP002277420, & JP 08 092303 A, (Showa Sangyo Co), Apr. 9, 1996, Abstract.
Database WPI, Derwent Publications Ltd., London, GB, XP009029650, Apr. 18, 2001, Article.
Database WPI, Derwent Publications Ltd., London, GB, XP00928863, 1991, Article.
Hachimura et al., "Suppressive effect of dietary raffinose on T-helper 2 cell-mediated immunity", British Journal of Nutrition, vol. 88m No. 4, pp. 421-426, (Oct. 2002).
Hirayama, "Novel physiological functions of oligosaccharides", Pur Appl. Chem., vol. 74, No. 7, pp. 1271-1279 (2002).
Infante-Duarte et al., "Th1/Th2 balance in infection", Springer Semin. Immunopathol, vol. 21, pp. 317-338, (1999).
Miniello et al., "Prebiotics in infant milk formulas: new perspectives", Acta Paediatr Supp., vol. 441, pp. 68-76, (2003).

\* cited by examiner

*Primary Examiner* — Shaojia Anna Jiang
*Assistant Examiner* — Michael C Henry
(74) *Attorney, Agent, or Firm* — The Webb Law Firm

(57) ABSTRACT

The present invention relates to a method for enhancing the immune system and the treatment and/or prevention of immune system related disorders in a mammal, particularly newborns, said method comprising the administration of acid oligosaccharide and neutral oligosaccharide. Food compositions suitable for use in the above method are also provided.

13 Claims, No Drawings

IMMUNEMODULATING OLIGOSACCHARIDES

FIELD OF THE INVENTION

The present invention relates to a method for the treatment and/or prevention of immune diseases, said method comprising the administration of oligosaccharides.

BACKGROUND OF THE INVENTION

The immune system has different possible ways of reacting to an antigen. A decisive step for the type of immune response is the stimulation of different T-cell subpopulations. So called Th1 cells predominantly produce cytokines, which stimulate a cellular immune response (IFN-γ, IL-12, IL-2). In contrast, Th2 cells predominantly produce IL-4, IL-5 and IL-0. These cytokines boost an IgE-mediated allergic reaction and inflammation and are thought as well to be involved with recruitment, proliferation, differentiation, maintenance and survival of eosinophils (i.e., leukocytes that accept an eosin stain), which can result in eosinophilia. Eosinophilia is a hallmark of many Th2 mediated diseases, such as asthma, allergy, and atopic dermatitis. Th1- and Th2-related cytokines act antagonistically and the Th1/Th2 responses are under normal physiological circumstances in a well-controlled balance. Neither the Th1 nor the Th2 response prevails. If in disbalance, the dominance of one of Th1 or Th2 immune responses play a role in or is responsible for several pathological conditions.

An excessive Th 1 immune response eventually can lead to autoimmunity, the breakdown of material of the individuals own body, e.g. insulin dependent diabetes mellitus, multiple sclerosis, Crohn's disease, Pemphigus vulgaris, autoimmune thrombocytopenic purpura, autoimmune hemolytic anemia.

An excessive Th 2 response leads to extreme sensitivity towards foreign components which should not lead to any immunological reaction, e.g. allergies and related diseases such as atopic dermatitis, asthma, occupational asthma, food allergy (e.g. cows milk allergy, apple allergy, peanut and other nut allergies, lupine allergy), allergic rhinitis (e.g. pollen allergy), dust mite allergy and other forms of hypersensitivity like systemic anaphylaxis and acute urticaria.

A relative shift towards an increased Th 2 response and/or reduced Th1 response is found under circumstances of stress of any sort, which consequently results in a bias towards a Th 2 response. Such relative shift is for example observed in immunosenescence, cancer patients, chronic infections, an overload of exercise, social conflicts or high work loads, exposure to toxic components or radiation and metabolic stress leading to malnutrition, cachexia or malnutrition caused by anorexia. (Janeway (2001) Immunobiology $5^{th}$ edition, Garland publishing ISBN 0-8153-3642-x; Roitt et al (2001) Immunology $6^{th}$ edition, Harcourt publishing limited, ISBN-0-7234-31892).

Bifidogenic effects are held responsible for e.g. reduction and/or prevention of bacterial infection. It is known that oligosaccharides can display bifidogenic effects.

Acid oligosaccharides have been described to have advantageous effects. WO 02/42484 describes esterified pectin hydrolysates for the treatment of infection and/or the prevention of adhesions of harmful substances to eukaryotic cells. DE 4223613 describes a process for the preparation of unsaturated uronides from pectin-like substances through anaerobic fermentation, using e.g pectate lyase. The preparation can be used for the medical treatment of heavy metal intoxication.

Also combinations of acid- and neutral oligosaccharides have been described. EP 1105002 describes a prebiotic composition comprising transgalactooligosaccharides, inulin and galacturonic acid oligosaccharides. U.S. Pat. No. 6,576,251 describes a combination of sialyated oligosaccharide (di-sialolacto-N-tetraose) and galactooligosaccharides, for the prophylaxis of symptoms connected with the adhesion of organisms such as influenza WO 01/60378 describes mixtures of unsaturated pectin hydrolysate and neutral oligosaccharides for the prevention of adhesion of pathogens to epithelial surfaces.

Infant formulae containing lipid, protein, saccharides, vitamin and at least one selected from di- or higher saccharide containing galactose, a derivative thereof, saccharide containing N-acetylneuraminic acid and a derivative thereof are known (EP 1332759).

SUMMARY OF THE INVENTION

Until now it has been assumed that administration of (acid) oligosaccharides provides an advantageous effect by stimulating bifidogenic flora, and preventing adhesion of pathogens to the epithelial tissues.

The present inventors have now surprisingly found that systemic markers for the function of the immune system are influenced by the administration of (acid) oligosaccharides. This finding opens a new field of application of oligosaccharides, particularly for diseases which at best can be treated by immune system modulation. By "modulation" or "modulating" is intended an increase or decrease in a particular character, quality, activity, substance or response. In other words, it has surprisingly been found that acid oligosaccharides and neutral oligosaccharides are capable of stimulating the systemic immune response.

The present inventors also surprisingly found that the different oligosaccharides have different stimulatory effects on the immune system. It was found that administration of acid oligosaccharides (relatively) stimulates Th1 response and lowers the Th2 cytokine release (e.g. IL-10, IL-4 and IL-5). It was also found that administration of a combination of acid oligosaccharide and neutral oligosaccharide synergistically stimulates the immune-system, particularly by lowering the Th2 response and increasing the Th1 response.

In a further aspect of the present invention it was found that oligosaccharides can be advantageously used to restore disbalance in the Th1/Th2 responses and for the treatment and prevention of disorders which are associated with Th1/Th2 disbalance.

In particular, it was surprisingly found that the administration of acid oligosaccharide, combined with neutral oligosaccharide, is able to restore Th1/Th2 disbalance and/or maintain a favorable Th1/Th2 balance. It was also found that acid oligosaccharide, in combination with the neutral oligosaccharide is capable of stimulating Th1 response. The present inventors also believe that the administration of acid- and neutral oligosaccharides stimulates Th3, i.e. enhances the regulatory T cell activity. It is perceived that the stimulation of Th1 response is achieved in part by inhibiting Th2 response.

Hence, the present invention comprises administering an acid- and neutral oligosaccharide, more preferably acid oligosaccharide and two chemically distinct neutral oligosaccharides in a method for
    modulating the immune system;
    stimulating the development of the immune system, particularly in humans of the age between 0-1 year;
    enhancing systemic immune response;
    treatment and/or prevention of Th1/Th2 disbalance; and/or treatment and/or prevention of diseases which at best can be treated by immune-system modulation.

In other words it can thus be said that acid oligosaccharide has a beneficial effect on inflammatory cytokines (Th1 response). In addition the combination of acid oligosaccharide and neutral oligosaccharide has a beneficial effect on inflammatory cytokines (Th2 response).

DETAILED DESCRIPTION

The present invention relates to a method for the treatment and/or prevention of an immune system related disorder in a mammal, said method comprising administering to said mammal a composition comprising a therapeutically effective amount of acid oligosaccharide and neutral oligosaccharide, i.e. the use of acid oligosaccharide and neutral oligosaccharide in the manufacture of a composition for the treatment and/or prevention of an immune system related disorder in a mammal.

In a further aspect, the present invention relates to the use of acid oligosaccharide and neutral oligosaccharide in the manufacture of a composition for enhancing the immune response in a mammal and/or a method for modulating the immune system.

In yet a further aspect, the present invention relates to a food composition comprising between 5 and 50 en % lipid, between 10 and 60 en % protein, between 15 and 90 en % carbohydrate, and preferably a caloric density between 0.5 and 2 kcal/ml, acid oligosaccharide and neutral oligosaccharide, wherein said acid oligosaccharide comprises at least one terminal uronic acid unit; and
said neutral oligosaccharide is selected from the group consisting of cellobiose, cellodextrin, B-cyclodextrin, indigestible dextrin, gentiooligosaccharide, glucooligosaccharide, isomaltooligosaccharide, isomaltose, isomaltriose, panose, leucrose, palatinose, theanderose, D-agatose, D-lyxo-hexulose, lactosucrose, α-galactooligosaccharide, β-galactooligosaccharide, transgalactooligosaccharide, lactulose, 4'-galatosyllactose, synthetic galactooligosaccharide, fructans—Levan-type, fructans—Inulin-type, 1 f-β-fructofuranosylnystose, xylooligosaccharide, lafinose, lactosucrose and arabinooligosaccharide.

In a further aspect the present invention relates to a method for the treatment and/or prevention of an immune system related disorder selected from autoimmune disorders, hereditary or conditional induced immunodeficiency, support for vaccinations, allergy Type 1, allergy Type 2 and allergy Type 3, said method comprising administering to said mammal a composition comprising a therapeutically effective amount of acid oligosaccharide.

Some diseases that are thought to be caused/mediated in substantial part by Th2 immune response, IL-4/IL-5 cytokine induction, and/or eosinophilia (and accordingly responsive to treatment according to the present invention) include asthma, allergic rhinitis, systemic lupus erythematosis, Ommen's syndrome (hypereosinophilia syndrome). These are examples of non-viral and non-tumor, Th2 mediated diseases for which effective treatment with the method of the present invention clearly could not have been predicted. Particularly preferred methods of the present invention are for the treatment of diseases associated with eosinophilia, such as asthma and allergic rhinitis.

A therapeutically effective amount for a particular disorder can be routinely determined by one of skill in the art via dose-finding studies.

Immune System Related Disorder

It has now been found that the administration of acid oligosaccharide, preferably combined with neutral oligosaccharide provides beneficial systemic effects to the subject. Systemic means affecting the entire body as a result of the (systemic) circulation of the blood and/or lymph.

In one aspect, the present invention provides a method for modulating and/or enhancing the immune system, said method comprising the administration of acid- and neutral oligosaccharides. This method can be suitably used in a method for balancing the Th1/Th2 response, in particular by simulating the Th1 response. Hence, compositions containing the present oligosaccharide(s) which are advertised to e.g. simulate maturation of the immune system, enhance the resistance to pathogens by enhancing the immune system and/or support the immune system are part of the present invention.

In a further aspect, the present invention provides a method for the treatment and/or prevention of an immune system related disorder, said method comprising administering to said mammal a composition comprising a therapeutically effective amount of acid oligosaccharide.

The acid oligosaccharide of the present invention has a degree of polymerization between 1 and 250 and is prepared from pectin or alginate.

In a further aspect, the present invention provides a method of enhancing the immune response in a mammal said method comprising administering to the mammal a composition comprising acid oligosaccharide, optionally combined with neutral oligosaccharide.

It was particularly surprising that the enteral administration of the present oligosaccharides provides the beneficial systemic effects. Hence, the present method preferably comprises the enteral, even more preferably the oral administration of acid- and neutral oligosaccharide.

In a further embodiment, the method of the invention relates to the administration of oligosaccharides to infants, preferably humans in the age of 0 to 6 years, preferably in the age of between 0 and 1 year. As this group has a particular disbalance in the Th1/Th2 ratio (the Th2 prevails in many cases), the present method can be suitably used to restore this disbalance in this population. Administration of the acid oligosaccharide, preferably combined with the neutral oligosaccharide is also believed to improve maturation of the (gastro) intestinal tract of the newborns, making the present method and composition particularly suitable for administration to pre-term infants. In a preferred embodiment the present method relates to the stimulation of the maturation of the immune system in human subjects between the age of 0-6 year, preferably between 0 and 1 year.

Further preferred compositional features such as protein, carbohydrate, lipid, osmolality, viscosity and caloric density of a composition which can be suitably used in this method are described below.

The immune system related disorder is preferably selected from autoimmune disorders, hereditary or conditional induced immunodeficiency, support for vaccinations, allergy Type 1, allergy Type 2, allergy Type 3 and allergy Type 4.

Autoimmune disorders which can suitably be treated include systemic lupus erythematosus, chronic glomerulonephritis, polyarteritis nodosa, poststreotococcal acute glomerulonephritis, Graves' disease, myasthenia gravis, insulin resistant diabetes, hashimoto's thyroiditis, hemolytic anemia, pernicious anemia, Goodpasture's syndrome, pemphigus vulgaris, autoimmune thrombocytopenia purpura, acute rheumatic fever, mixed essential cryoglobulinemic, autoimmune pernicious anemia, autoimmune Addison's disease, Vitiligio, hypoglycemia, neonatal lupus rash, IDDM (insulin dependent diabetes mellitus), rheumatoid arthritis, multiple sclerosis, psoriasis, scleroderma, Crohn's disease, IBD (inflammatory bowel disease), neuropathy, preferably insulin resistant diabetes Conditions of hereditary or conditional induced immunodeficiency which can suitably be treated include immunosenescence, autism, malnutrition caused by chronic diseases, such as cancer, COPD (chronic obstructive pulmonary disease), AIDS, arthritis, diabetes, anorexia, cachexia, dysphagia, kidney failure, radiation, patients suffering from chronic ulcerations and stress in more detail stress after social stress, chronic infection or cigarette smoke, air pollution, radiation, chemotherapy.

Because stimulation of the immune system is of particular importance in subjects suffering from Acquired Immunodeficiency Syndrome (AIDS) and/or Human Immunodeficiency Virus (HIV) Infection, in a preferred embodiment the present invention particularly provides a method for the treatment and/or prevention AIDS and/or HIV infection, said method comprising the enteral administration of the present acid oligosaccharides, preferably in combination with the present neutral oligosaccharides. The present invention also provides a method for the treatment and/or prevention of diarrhea in subjects suffering from AIDS and/or HIV infection, said method comprising enterally administering the present acid oligosaccharides, preferably in combination with the present neutral oligosaccharides. The present (acid) oligosaccharide is preferably provided to the subject suffering from AIDS and/or HIV infection in a nutritional matrix, i.e. a composition comprising fat, protein and carbohydrate.

Allergies which can suitably be treated include Type 1 allergies; atopy, asthma, hay fever, eczema, food allergy, drug allergy. Type 2 allergies; hemolytic disease of new borns, autoimmune hemolytic anemia, ankylosing spondylitis, acute anterior uveitis. Type 3 allergies; arthus reaction, serum sickness. Type 4 allergies: delayed type hypersensitivity, contact sensitivity, celiac disease.

It was also found that the present method can suitably be used to support vaccination processes, e.g. enhance the effects of a vaccination process. These are included in the term immune system related disorders. The acid oligosaccharides, preferably combined with the neutral oligosaccharides, are preferably (orally) administered before, during and/or after vaccination. Particularly the effects of vaccinations for diptheria-tetanus-pertussis, polio vaccine, measles/mumps/rubella, pneumococcal conjugate, haemophilus B conjugate, hepatitis B, hepatitis A, varicella, influenza can suitably be enhanced.

Preferably the present method relates to the treatment and/or prevention of malnutrition, atopy, asthma or COPD.

The present invention also relates to the use of acid oligosaccharides in the manufacture of a composition for the treatment and/or prevention of an immune system related disorder selected from autoimmune disorders, hereditary or conditional induced immunodeficiency (preferably not AIDS), support for vaccinations, allergy Type 1, allergy Type 2 and allergy Type 3.

Acid Oligosaccharides

The term acid oligosaccharide refers to oligosaccharides comprising at least one acidic group selected from the group consisting of N-acetylneuraminic acid, N-glycoloylneuraminic acid, free or esterified carboxylic acid, sulfuric acid group and phosphoric acid group. The acid oligosaccharide preferably is a polyhexose. Preferably, at least one of the aforementioned acid groups is situated at the terminal hexose unit of the acid oligosaccharide. Preferably the acid oligosaccharide has the structure as depicted in FIG. 1, wherein the terminal hexose (left) preferably comprises a double bond. Preferably the acid oligosaccharide contains a carboxylic acid at the terminal hexose unit, wherein said carboxylic acid group may be free or esterified. Methods for the manufacture of esterified pectin hydrolysates that can be suitably used in the present method and composition are provided in WO 01/60378 and/or WO02/42484, which are hereby incorporated by reference.

The hexose units other than the terminal hexose unit(s) are preferably uronic acid units, even more preferably galacturonic acid units. The carboxylic acid groups on these units may be free or (partly) esterified, and preferably at least 10% is methylated (see below).

FIG. 1. Polymeric acid oligosaccharide

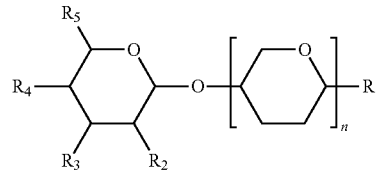

wherein:

R is preferably selected from the group consisting of hydrogen, hydroxy or acid group, preferably hydroxy; and at least one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloylneuraminic acid, free or esterified carboxylic acid, sulfuric acid group or phosphoric acid group, and the remaining represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ representing hydroxy and/or hydrogen; and n is an integer and refers to a number of hexose units (see also Degree of Polymerisation, below), which may be any hexose unit. Suitably n is an integer between 1-5000. Preferably the hexose unit(s) is an uronic acid unit.

Most preferably $R_1$, $R_2$ and $R_3$ represent hydroxy, $R_4$ represent hydrogen, $R_5$ represents carboxylic acid, n is any number between 1 and 250, preferably between 1 and 10 and the hexose unit is galacturonic acid.

The detection, measurement and analyses of the preferred acid oligosaccharides as used in the present method are given in applicant's earlier patent application relating to acid oligosaccharides, i.e. WO 0/160378, which is hereby incorporated by reference.

Preferably, the acid oligosaccharide has one, preferably two, terminal uronic acid units, which may be free or esterified. Preferably the terminal uronic acid unit is selected from the group consisting of galacturonic acid, glucuronic acid, guluronic acid, iduronic acid, mannuronic acid, riburonic acid and alturonic acid. These units may be free or esterified. In an even more preferred embodiment, the terminal hexose unit has a double bond, which is preferably situated between the $C_4$ and $C_5$ position of the terminal hexose unit. Preferably one of the terminal hexose units comprises the double bond. The terminal hexose (e.g. uronic acid) preferably has a structure according to FIG. 2.

FIG. 2: Preferred terminal hexose acid group

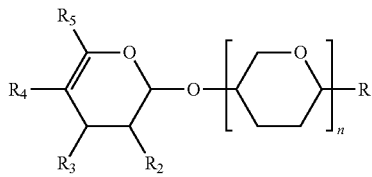

wherein;
R is preferably selected from the group consisting of hydrogen, hydroxy or acid group, preferably hydroxy (see above); and
at least one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ represent hydroxy and/or hydrogen; and n is an integer and refers to a number of hexose units (see also Degree of Polymerisation, below), which may be any hexose unit. Suitably n is an integer between 1-5000 representing the number of hexose units said hexose units preferably being uronic acid, even more preferably being galacturonic acid units. The carboxylic acid groups on these units may be free or (partly) esterified, and are preferably at least partly methylated. Most preferably, $R_2$ and $R_3$ represent hydroxy, $R_4$ represent hydrogen and $R_5$ represents free or esterified carboxylic acid.

In a further embodiment, a mixture of acid oligosaccharides is used, which have a different DP and/or comprise both unsaturated and saturated terminal hexose unit. Preferably at least 5%, more preferably at least 10%, even more preferably at least 25% of the terminal hexose units of the acid oligosaccharide unsaturated hexose unit (see e.g. FIG. 2). As each individual acid oligosaccharide preferably comprises only one unsaturated terminal hexose unit, preferably no more than 50% of the terminal hexose units is an unsaturated hexose unit (i.e. comprises a double bond).

A mixture of acid oligosaccharides preferably contains between 2 and 50% unsaturated hexose units based on the total amount of hexose units, preferably between 10 and 40%.

The acid oligosaccharide as used in the present method has a degree of polymerisation (DP) between 1 and 5000, preferably between 1 and 1000, more preferably between 2 and 250, even more preferably between 2 and 50, most preferably between 2 and 10. If a mixture of acid oligosaccharides with different degrees of polymerisation is used, the average DP of the acid oligosaccharide mixture is preferably between 2 and 1000, more preferably between 3 and 250, even more preferably between 3 and 50. See also FIG. 1, wherein the sum of "n" and the terminal unit (i.e. n+1) represents the degree of polymerisation. It was found that a lower DP of the oligosaccharides improves the palatability and results in a reduced viscosity product if the acid oligosaccharide is administered in liquid form. The acid oligosaccharide may be a homogeneous or heterogeneous carbohydrate.

The acid oligosaccharides used in the invention are preferably prepared from pectin, pectate, alginate, chondroitine, hyaluronic acids, heparine, heparane, bacterial carbohydrates, sialoglycans, fucoidan, fucooligosaccharides or carrageenan, preferably from pectin or alginate. The acid oligosaccharides may be prepared by the methods described in WO 01/60378, which is hereby incorporated by reference.

Alginates are linear unbranched polymers containing β-(1→4)-linked D-mannuronic acid and α-(1→4)-linked L-guluronic acid residues with a wide range of average molecular weights (100-100000 residues). Suitable sources of alginate include seaweeds and bacterial alginates.

Pectin is divided into two main categories: high methoxylated pectin, which is characterised by a degree of methoxylation above 50% and low methoxylated pectin having a degree of methoxylation below 50%. As used herein, "degree of methoxylation" (also referred to as DE or "degree of esterification") is intended to mean the extent to which free carboxylic acid groups contained in the polygalacturonic acid chain have been esterified (e.g. by methylation). The present acid oligosaccharide is preferably prepared from high methoxylated pectin.

The acid oligosaccharides are preferably characterised by a degree of methoxylation above 20%, preferably above 50% even more preferably above 70%. Preferably the acid oligosaccharides have a degree of methylation above 20%, preferably above 50% even more preferably above 70%.

The acid oligosaccharide is preferably administered in an amount of between 10 mg and 100 gram per day, preferably between 100 mg and 50 grams per day, even more between 0.5 and 20 gram per day.

Neutral Oligosaccharides

The term neutral oligosaccharides as used in the present invention refers to saccharides which have a degree of polymerisation of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide.

The term neutral oligosaccharides as used in the present invention preferably refers to saccharides which have a degree of polymerisation of the oligosaccharide below 60 monose units, preferably below 40, even more preferably below 20, most preferably below 10.

The term monose units refers to units having a closed ring structure, preferably hexose, e.g. the pyranose or furanose forms.

The neutral oligosaccharide preferably comprises at least 90%, more preferably at least 95% monose units selected from the group consisting of mannose, arabinose, fructose, fucose, rhamnose, galactose, β-D-galactopyranose, ribose, glucose, xylose and derivatives thereof, calculated on the total number of monose units contained therein.

Suitable neural oligosaccharides are preferably fermented by the gut flora. Preferably the oligosaccharide is selected from the group consisting of:
cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxohexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactoseI, II and III), fructans— Levan-type (β-D-(2→6)-fructofuranosyl)$_n$ α-D-glucopyranoside), fructans—Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably the neutral oligosaccharide is selected from the group consisting of fructooligosaccharides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands) the entire content of which is hereby incorporated by reference.

Transgalactooligosaccharides (TOS) are for example sold under the trademark Vivinal™ (Borculo Domo Ingredients, Netherlands).

Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes.

Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment the present method comprises the administration of 2 chemically distinct oligosaccharides. It was found that the administration of acid oligosaccharides combined with two chemically distinct neutral oligosaccharides provides an optimal effect. Preferably the present method comprises the administration of an

- acid oligosaccharides (see above);
- galactose based neutral oligosaccharide (>50% of the monose units are galactose), preferably selected from the group consisting of galactooligosaccharide and transgalactooligosaccharide; and
- fructose and/or glucose based neutral oligosaccharides (>50% of the monose units are fructose and/or glucose, preferably fructose), preferably inulin, fructan and/or fructooligosaccharide, most preferably long chain fructooligosaccharide (average DP between 10 and 60).

This composition is particularly suited for administration to infants in the age between 0-1 year.

In a further embodiment, the present method comprises the administration of 2 structurally (chemically) distinct oligosaccharides, wherein two structurally (chemically) distinct oligosaccharides are differentiated by their type of glycosidic linkages.

Preferably the method comprises the administration of two chemically distinct neutral oligosaccharides, said chemically distinct oligosaccharides having a different DP and/or different average DP, preferably different average DP. In another embodiment administering chemically distinct neutral oligosaccharides with different average DP, provides an even more optimal immune-modulating effect. Preferably galactose based neutral oligosaccharide has an average DP between 2 and 10, and fructose and/or glucose based neutral oligosaccharides have an average DP between 10 and 60.

The neutral oligosaccharide is preferably administered in an amount of between 10 mg and 100 gram per day, preferably between 100 mg and 50 grams per day, even more preferably between 0.5 and 20 gram per day.

Synergistic Effect Acid and Neutral Oligosaccharides

The acid- and neutral oligosaccharides were found to have a synergistic immune stimulatory effect. Hence, preferably the present method comprises the administration of a therapeutically effective amount of acid oligosaccharides and neutral oligosaccharides.

The mixture of acid- and neutral oligosaccharides is preferably administered in an amount of between 10 mg and 100 gram per day, preferably between 100 mg and 25 grams per day, even more preferably between 0.5 and 20 gram per day.

A preferred combination of acid oligosaccharides and neutral oligosaccharides comprises the acid oligosaccharides of FIG. 2, wherein R represents hydrogen, hydroxy or acid group, preferably hydroxy; and one selected from the group consisting of $R_2$, $R_3$, $R_4$ and $R_5$ represents free or esterified carboxylic acid and the remaining of $R_2$, $R_3$, $R_4$ and $R_5$ represent hydroxy and/or hydrogen; and galactooligosaccharide and/or transgalactooligosaccharide.

Preferably the acid and neutral oligosaccharides are administered in a weight ratio of between 0.01:1 and 1:0.01, preferably in a weight ratio of between 0.1:1 and 1:0.1.

LCPUFA

In a preferred embodiment, the present method further comprises the administration of long-chain polyunsaturated acid (LCPUFA). As it is believed that these act on the immune system via a mechanism different from the acid oligosaccharides or neutral oligosaccharides, the oligosaccharides combined with the LCPUFA is deemed to act synergistically. The present method preferably comprises the administration of between 0.1 and 100 g LCPUFA per day, more preferably between 1 and 25 grams LCPUFA per day.

Foods

It was found that the acid oligosaccharides, and particularly the synergistic mixture of acid and neutral oligosaccharides can be advantageously applied in food, such as baby food and clinical food. Such food preferably comprises lipid, protein and carbohydrate and is preferably administered in liquid form. The term. "liquid food" as used in the present invention includes dry food (e.g. powders) which are accompanied with instructions as to admix said dry food mixture with a suitable liquid (e.g. water).

Hence, the present invention also relates to a nutritional composition which preferably comprising between 5 and 50 en % lipid, between 10 and 60 en % protein, between 15 and 90 en % carbohydrate and the present acid oligosaccharides, preferably in combination with the neutral oligosaccharides. Preferably the present nutritional composition preferably contains between 10 and 30 en % lipid, between 15 and 40 en % protein and between 25 and 75 en % carbohydrate (en % is short for energy percentage and represents the relative amount each constituent contributes to the total caloric value of the preparation).

Such food preferably is in liquid form and has a limited viscosity. It was found that the foods containing the acid oligosaccharides, optionally combined with the neutral oligosaccharides, provides a liquid nutrition with sufficiently low viscosity so it can be applied as e.g. liquid baby foods and liquid clinical food which can be fed through a tube or a straw, while retaining the low viscosity. In a preferred embodiment, the present composition has a viscosity below 600 mPas, preferably below 250 mPas, more preferably below 50 mPas, most preferably below 25 mPas at a shear rate of $100^{-1}$ at 20° C. Whenever the term viscosity used in the present document, this refers to the physical parameter which is determined according to the following method:

The viscosity may be determined using a Carri-Med CSL rheometer. The used geometry is of conical shape (6 cm 2 deg acrylic cone) and the gap between plate and geometry is set on 55 μm. A linear continuous ramp shear rate is used from 0 to 150 $s^{-1}$ in 20 seconds.

Preferably vegetable lipids are used. The vegetable lipid is preferably at least one selected from the group consisting of soy oil, palm oil, coconut oil, safflower oil, sunflower oil, corn oil, canola oil and lecithins. Animal fats such as milk fats may also be added if desired.

The proteins used in the nutritional preparation are preferably selected from the group of non-human animal proteins (such as milk proteins, meat proteins and egg proteins), vegetable proteins (such as soy protein, wheat protein, rice protein, and pea protein), free amino acids and mixtures thereof. Cow milk proteins such as casein and whey proteins are particularly preferred.

A source of digestible carbohydrate may be added to the nutritional formula. It preferably provides about 40% to about 80% of the energy of the nutritional composition. Any suitable (source of) carbohydrate may be used, for example sucrose, lactose, glucose, fructose, corn syrup solids, and maltodextrins, and mixtures thereof.

The present composition is preferably substantially free of viable bifinogenic bacteria.

Stool irregularities (e.g. hard stools, insufficient stool volume, diarrhea) is a major problem in many babies and ill subjects that receive liquid foods. It was found that stool problems may be reduced by administering the present oligosaccharides in liquid food which have an osmolality between 50 and 500 mOsm/kg, more preferably between 100 and 400 mOsm/kg.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml.

Infant Formula

It was found that the present composition can be advantageously applied for infant formula. Such infant formula preferably comprises lipid, protein and carbohydrate and is preferably administered in liquid form. The term "liquid food" as used in the present invention includes dry food (e.g. powders) which are accompanied with instructions as to admix said dry food mixture with a suitable liquid (e.g. water).

Hence, the present invention also relates to an infant formula which preferably comprises between 5 and 60 en % lipid, between 5 and 40 en % protein, between 15 and 90 en % carbohydrate and the present combination of oligosaccharides and LC-PUFA's. Preferably the present infant formula contains between 30 and 60 en % lipid, between 6 and 15 en % protein and between 25 and 75 en % carbohydrate (en % is short for energy percentage and represents the relative amount each constituent contributes to the total caloric value of the preparation).

Preferably a combination of vegetable lipids and at least one oil selected from the group consisting of fish oil and omega-3 containing vegetable, algae or bacterial oil is used.

The proteins used in the nutritional preparation are preferably selected from the group of non-human animal proteins (such as milk proteins, meat proteins and egg proteins), vegetable proteins (such as soy protein, wheat protein, rice protein, and pea protein), free amino acids and mixtures thereof. Cow milk derived nitrogen source, particularly cow milk protein proteins such as casein and whey proteins are particularly preferred.

A source of digestible carbohydrate may be added to the nutritional formula. It preferably provides about 40% to about 80% of the energy of the nutritional composition. Any suitable (source of) carbohydrate may be used, for example sucrose, lactose, glucose, fructose, corn syrup solids, and maltodextrins, and mixtures thereof.

According to a particularly preferred embodiment, the present infant formula contains 7 to 12 energy % protein; 40 to 55 energy % carbohydrates; and 35 to 50 energy % fat. As this composition is particularly suitably used to reduce the allergic reaction in an infant, the protein of the infant formula is preferably selected from the group consisting of hydrolyzed milk protein (e.g. hydrolyzed casein or hydrolyzed whey protein), vegetable protein and/or amino acids. The use of these proteins further reduced the allergic reactions of the infant.

Stool irregularities (e.g. hard stools, insufficient stool volume, diarrhea) is a major problem in many babies that receive liquid foods. It was found that stool problems (e.g. diarrhea) may be reduced by administering the present oligosaccharides in liquid food which have an osmolality between 50 and 500 mOsm/kg, more preferably between 100 and 400 mOsm/kg.

In a particularly preferred embodiment, the present invention also provides a composition which is particularly suitable for use in the present method. This composition has a high similarity with natural human milk, both in functionality and molecular structure. Hence, the composition is particularly suitable as an infant formula. The present composition contains fat, carbohydrate, protein; and between 0.5 and 1 gram soluble indigestible oligosaccharides per 100 ml liquid product, preferably between 0.7 and 0.9 gram/100 ml. Furthermore the composition contains, per 100 ml liquid product, between 0.4 and 0.7 gram transgalactooligosaccharides (indigestible [galactose]$_n$-glucose comprising β-linked saccharides; wherein n is an integer between 1 and 60, i.e. 2, 3, 4, 5, 6 . . . , 59, 60; preferably n is selected from 2, 3, 4, 5, 6, 7, 8, 9, or 10); and between 0.01 and 0.1 gram inulin (indigestible polysaccharide carbohydrate comprising a chain of at least 10 β-linked fructose units); and between 0.04 and 0.3 gram acid oligosaccharides as depicted in FIG. 2. The present liquid product can be suitably prepared by a consumer from a powdered product. The present liquid product preferably contains the ingredients and has the characteristics as described herein above and below and can be favorably used in the methods described herein.

Oligosaccharides

The acid oligosaccharide is preferably included in the present composition according to the invention in an amount exceeding 0.1 wt. %, preferably exceeding 0.2 wt. %, more preferably exceeding 0.5 wt. % and even more preferably exceeding 1 wt. % based on the total dry weight of the composition. Although the administration of considerable amounts of oligosaccharides will generally not lead to undesirable side effects, the present composition preferably has an oligosaccharide content below 20 wt. %, more preferably below 10 wt. % even more preferably below 5 wt. %.

The neutral oligosaccharide is preferably included in the present composition according to the invention in an amount exceeding 0.1 wt. %, preferably exceeding 0.2 wt. %, more preferably exceeding 0.5 wt. % and even more preferably exceeding 1 wt. % based on the total dry weight of the composition. Although the administration of considerable amounts of oligosaccharides will generally not lead to undesirable side effects, the present composition preferably has an oligosaccharide content below 20 wt. %, more preferably below 10 wt. % even more preferably below 5 wt. %.

The present composition was found to synergistically stimulate the immune system. Hence, the present composition can be suitably used in a method for the treatment and/or prevention of infection, said method comprising orally administering to a human, preferably an infant, the present composition. By stimulating the immune system and by promoting a healthy intestinal flora, the present composition also has a systemic anti-infective effect. Hence, the present acid oligosaccharides, preferably combined with the present neutral oligosaccharides can be advantageously used for the treatment and/or prevention of intestinal infections and/or respiratory tract infections. In a further preferred embodiment the oligosaccharide(s) are orally administered in a food matrix as described above.

Because stimulation of the immune system is of particular importance in subjects suffering from cancer, in particular those patients that are or have been subjected to chemotherapy, radiation and those patients that are cachectic (as typically occurs in the terminal phase of cancer), the present invention provides a method for the treatment of these subjects, said method comprising the enteral administration of the present acid oligosaccharides, preferably in combination with the present neutral oligosaccharides. The present (acid) oligosaccharide is preferably provided to these subjects in a nutritional matrix, i.e. a composition comprising fat, protein and carbohydrate.

EXAMPLES

Example 1

Experimental Setup

The effect of diets comprising acid oligosaccharides, optionally combined with neutral oligosaccharides were tested on the delayed-type hypersensitivity (DTH) response, which is a parameter for Th1 immunological response and is determined by measuring the increase in ear swelling after local antigen challenge.

Acid oligosaccharides (AcOl) used, with an average DP between 2 and 10, were obtained by the method described in WO 02/42484 (see example 1). Diets containing 1 wt. %, 2.5 wt. %, 5 wt. % and 10% wt. % AcOl based on total weight of the diet were tested. Neutral oligosaccharide mixture (GF) containing galactooligosaccharides (GOS) (Vivinal-GOS™ (Borculo Domo Ingredients, Netherlands) and fructooligosaccharides (FOS) (Raftiline HP™, Orafti, Tienen, Belgium) were used in a weight ratio GOS:FOS of 9:1. Diets containing 1, 2.5 and 5 wt. % GF based on total weight of the diet were tested. The effects of a combination of acid and neutral oligosaccharides (GF and AcOl) was tested in a diet containing 1 wt. % GF and 1 wt. % AcOl based on total weight of the diet.

All data is presented as percentages relative to control values, i.e. the relative values of the oligosaccharide supplemented group compared to the group receiving the control diet (without oligosaccharides).

Animals and Diets

Female, 6 weeks old C57Bl/6 mice (Harlan Nederland BV, Horst, the Netherlands) were group-housed under a regular 12 hours light/dark regime. Group size was 10 animals per group and 3 animals in the negative control groups. The animals were given semi-synthetic diets (Research Diet Services, Wijk bij Duurstede, the Netherlands). Control diets were made to the AIN93G specifications (Reeves et al (1993) Development and Testing of the AIN93 purified diets for rodents: results on growth kidney calcification and bone mineralisation in rats and mice. J Nutrition 123(11): 1923-31), oligosaccharide supplemented diets were based on these specifications. Carbohydrate content of the supplemented diets were kept constant by the exchange of total carbohydrates for the oligosaccharides on a weight basis. The separate carbohydrate components were substituted respective to their normal ratio in the diet. The carbohydrates in the normal diet consist of cornstarch (40% of total weight), dextrinized cornstarch (13.2%), sucrose (10%) and cellulose (5%).

Vaccination Protocol

Vaccinations were started after a period of two to four weeks of adaptation to the new housing and diets. At day 0, a blood sample was collected prior to vaccination. At day 1, the first vaccination was administered subcutaneously. After three weeks, a blood sample was collected (day 21) and a booster vaccination was given (day 22). Nine days after booster injection (day 31), basal ear thickness was measured with a Digimatic outside micrometer (Mitutoyo, Veenendaal, the Netherlands) and a delayed-type hypersensitivity (DTH) response was induced by injecting antigen solution i.e. (intracutaneous) in the mouse ear pinnae. 24 h thereafter (day 32), the DTH response was measured, a bloodsample was taken and the mice were sacrificed. Spleens were isolated and prepared for ex-vivo restimulations.

The vaccinations consisted of a 100 μl i.e. (intracutaneous) injection of a 1:1 mix of antigen solution and Stimune adjuvant (Specol, Cedi-diagnostics BV, Lelystad, the Netherlands). The antigen solution was a 1:100 dilution of Influvac 2002/2003 (Solvay Pharmaceuticals, Weesp, the Netherlands) in PBS. Influvac is a trivalent protein vaccine, containing 3×30 μg/ml hemagglutinin of three different influenza strains. For the DTH responses, mice were i.e. injected with 25 μl dialysed Influvac in both ears as a DTH challenge.

Cell Cultures

Splenocytes were isolated from the spleens using fine-mesh cell strainers (Becton Dickinson, Erembodegem, Belgium). Red blood cells were lysed by 5 minutes incubation on ice. After washing with culture medium without phenol red, cells were counted (Coulter Counter, Beckman Coulter, the Netherlands) and kept on ice. Cultures were set up using 0.1 μg/ml dialysed Influvac as a stimulus. Cells were seeded in 96-well culture plates at $1*10^6$ cells per well. The culture medium consisted of RPMI-1640 with HEPES buffer and 2 mM L-Glutamine (Invitrogen, Merelbeke, Belgium) with 10% fetal calf serum (FCS). Cultures were incubated for 5 days at 37° C. at 5% $CO_2$. Thereafter supernatants were harvested and frozen at −80° C. until analysis. Cell proliferation was measured in parallel cultures by $^3$H-thymidine incorporation, which was added to the cultures for the last 18 hours at 0.4 μCu/well. After 5 days, the cells were harvested using a Filtermate harvester (Perkin Elmer, Zaventem, Belgium) and counted on a Micro-Beta counter (Perkin Elmer, Zaventem, Belgium). Radioactive decay was measured for 1 minute per well and the counts per minute (cpm) were recorded as a measure for proliferation speed.

Cytokines were analysed in supernatants of Influvac stimulated cultures. IL-2, IL-5, IL-10 and IFN-gamma were measured using the Bio-Plex system with a custom mixed beadset for the cytokines mentioned (Bio-Rad, Veenendaal, the Netherlands). Cytokines were measured according to the manufacturer's specifications. IL-4 was measured by ELISA using the Pharmingen OptEIA mouse IL-4 kit (Becton Dickinson, Erembodegem, Belgium), according the manufacturer's specifications.

Results

DTH Response Acid Oligosaccharides

The diets containing dosages of 1 wt. %, 2.5 wt. % and 5 wt. % AcOl induced a statistically significant increase in the DTH response, showing a dose-dependent increase (see Table 1). The observed effect is indicative for the advantageous use of acid oligosaccharides in the present method.

TABLE 1

| Wt. % acid oligosaccharides in diet | DTH response (%) |
|---|---|
| 0 (controle) | 100 |
| 1 | 122 |
| 2.5 | 136* |
| 5 | 140* |

*indicates significantly different (P < 0.05) from control

DTH Response Acid and Neutral Oligosaccharides

The combination of 1 wt. % GF and 1 wt. % AcOl induce a statistically significant increase in the DTH (see Table 2). As the effect is significantly higher than the DTH responses from diets containing the acid or neutral oligosaccharides alone, these results are indicative for the synergistic effect provided by the administration of acid and neutral oligosaccharides. The observed effect is indicative for the advantageous use of a combination of acid and neutral oligosaccharides in the present method.

TABLE 2

| Wt. % oligosaccharides in diet | DTH response (%) |
|---|---|
| 0 (control) | 100 |
| 1 wt % GF | 132* |
| 1 wt. % AcOl | 122 |
| 2.5 wt % GF | 129* |

TABLE 2-continued

| Wt. % oligosaccharides in diet | DTH response (%) |
|---|---|
| 2.5 wt. % AcOl | 136* |
| 1 wt. % GF and 1 wt. % AcOl | 159* |

*indicates significantly different (P < 0.05) from control

Influvac Specific Proliferation of Acid Oligosaccharides

Administration of diets containing 2.5 wt % and 5 wt. % acid oligosaccharides (AcOl) induced a significant lowering effect on the influvac specific proliferation ex vivo (see Table 3). The observed effect is indicative for the advantageous use of acid oligosaccharides in the present method.

Influvac Specific Proliferation of a Combination of Acid and Neutral Oligosaccharides Administration of a combination of 1 wt. % GF and 1 wt. % AcOl induced significant lowering effects on the antigen specific proliferation (see Table 3). As the effect is significantly improved over the DTH responses from diets containing the acid or neutral oligosaccharides alone, these results are indicative for the synergistic effect provided by the administration of acid and neutral oligosaccharides. The observed effect is indicative for the advantageous use of a combination of acid and neutral oligosaccharides in the present method. Reduced proliferation is indicative for the reduction of Th2 response, and the Th1/Th2 balancing effect of the present method.

TABLE 3

| Wt. % oligosaccharides in diet | Influvac specific proliferation (%) |
|---|---|
| 0 (control) | 100 |
| 1 wt % GF | 100 |
| 1 wt. % AcOl | 92 |
| 2.5 wt. % AcOl | 61* |
| 5 wt. % AcOl | 54* |
| 1 wt. % GF and 1 wt. % AcOl | 50* |

*indicates significantly different (P < 0.05) from control

Th1/Th2 Balance: Cytokine Profiles after Administration of Acid Oligosaccharides Cytokine profiles were measured in the culture supernatants of the influvac specific splenocytes. Data are presented as percentage relative to values of the vaccinated control group (i.e. receiving no oligosaccharides). Compared to controls, diets containing 2.5 wt. % and 5 wt % AcOl resulted in a decrease in the Th2-related cytokines IL-4, IL-5 and IL-10, while the Th1-related cytokines IL-2 was increased and IFN-γ was not significantly lowered (see Table 4). These results are indicative for the Th1/Th2 balancing effect of acid oligosaccharides and indicative for the advantageous use of acid oligosaccharides in the present method, e.g. for the treatment and/or prevention of diseases with relatively low Th1 immunity.

Th1/Th2 Balance: Cytokine Profiles after Administration of Acid and Neutral Oligosaccharides Compared to controls, administration of a combination of 1 wt. % GT and 1 wt. % AcOl resulted in a decrease in the Th2-related cytokines IL-4, IL-5 and IL-10, while the Th1-related cytokines IL-2 and IFN-γ were not lowered (see Table 4, wherein data are presented as percentage relative to values of the vaccinated control group (i.e. receiving no oligosaccharides)). These results are indicative for the Th1/Th2 balancing effect of a combination of acid- and neutral oligosaccharides and indicative for the advantageous use of acid oligosaccharides in the present method, e.g. for the treatment and/or prevention of diseases with relatively low Th1 immunity. Particularly the IL-4/IFN ratio reflects the Th2/Th1 balance. In other words, a lower ratio is indicative for stimulation of Th1 and/or inhibition of Th2, and in any case indicative for the Th1-Th2 balancing effect of the present oligosaccharides.

TABLE 4

| Wt. % oligo-saccharides in diet | cytokine | | | | | |
| --- | --- | --- | --- | --- | --- | --- |
| | IFN-γ (%) | IL2 (%) | IL10 (%) | IL4 (%) | IL5 (%) | IL4/IFN-γ ratio |
| 0 (control) | 100 | 100 | 100 | 100 | 100 | 100 |
| 1 wt. % AcOl | 100 | 196* | 70 | 83 | 72 | 85 |
| 2.5 wt. % AcOl | 75 | 116 | 58* | 55 | 66 | 75 |
| 5 wt. % AcOl | 69 | 161* | 44* | 33* | 56* | 51* |
| 1 wt. % GF and 1 wt. % AcOl | 93 | 123 | 45* | 44* | 55* | 45* |

*indicates significantly different (P < 0.05) from control

The invention claimed is:

1. A method for the treatment of an immune system-related disorder selected from the group consisting of allergy Type 1, allergy Type 2, allergy Type 3, and allergy Type 4 in a mammal, comprising administering to said mammal a composition comprising a therapeutically effective amount of an acid oligosaccharide and at least two chemically distinct neutral oligosaccharides, wherein:
the acid oligosaccharide has a degree of polymerization between 1 and 250 and is prepared from pectin or alginate and comprises at least one terminal uronic acid unit selected from the group consisting of galacturonic acid, guluronic acid and mannuronic acid; and
the at least two chemically distinct neutral oligosaccharides comprise fructooligosaccharides and a second oligosaccharide selected from the group consisting of transgalactooligosaccharides, galactooligosaccharides and mixtures thereof.

2. The method according to claim 1, wherein the composition is administered enterally.

3. The method according to claim 1, wherein the composition is administered to a human in the age of 0-1 year.

4. The method according to claim 1, wherein the immune system related disorder is allergy Type 1.

5. The method according to claim 1, wherein the immune system related disorder is a Type 1 allergy selected from the group consisting of atopy, asthma, hay fever, eczema, food allergy and drug allergy.

6. The method according to claim 5, wherein the Type 1 allergy is atopy.

7. The method according to claim 5, wherein the Type 1 allergy is eczema.

8. The method according to claim 1, further comprising administering between 0.1 and 100 g of a long-chain polyunsaturated fatty acid per day.

9. The method according to claim 1, wherein the composition further comprises an infant formula comprising between 5 and 60 en % lipid, between 5 and 40 en % protein, between 15 and 90 en % carbohydrate and long chain polyunsaturated fatty acids.

10. The method according to claim 9, wherein the infant formula comprises 7 to 12 energy % protein, 40 to 55 energy % carbohydrates and 35 to 50 energy % fat.

11. The method according to claim 9, wherein the protein is selected from the group consisting of hydrolyzed milk protein, vegetable protein and/or amino acids.

12. The method according to claim 1, wherein the composition is a liquid food which has an osmolality between 50 and 500 mOsm/kg and/or a caloric density between 0.1 and 2.5 kcal/ml.

13. The method according to claim 1, wherein the immune system-related disorder is atopy in an infant.

* * * * *